US008700126B2

(12) United States Patent
Li et al.

(10) Patent No.: US 8,700,126 B2
(45) Date of Patent: Apr. 15, 2014

(54) SYSTEM AND METHOD FOR COMPUTER AIDED SEPTAL DEFECT DIAGNOSIS AND SURGERY FRAMEWORK

(75) Inventors: Shou Li, London (CA); Sukhdeep Gill, London (CA); Prakash Mahesh, Hoffman Estates, IL (US); Dave Roeder, Toronto (CA)

(73) Assignee: General Electric Company, Schenectady, NY (US)

( * ) Notice: Subject to any disclaimer, the term of this patent is extended or adjusted under 35 U.S.C. 154(b) by 2129 days.

(21) Appl. No.: 11/622,272

(22) Filed: Jan. 11, 2007

(65) Prior Publication Data
US 2008/0171933 A1 Jul. 17, 2008

(51) Int. Cl.
*A61B 5/05* (2006.01)

(52) U.S. Cl.
USPC ............ 600/413; 600/407; 600/410; 600/424

(58) Field of Classification Search
USPC .......... 600/407, 410, 413, 419, 425, 426, 428
See application file for complete search history.

(56) References Cited

U.S. PATENT DOCUMENTS

| | | | |
|---|---|---|---|
| 7,057,269 B2 | 6/2006 | Karnezos | |
| 7,061,088 B2 | 6/2006 | Karnezos | |
| 7,064,426 B2 | 6/2006 | Karnezos | |
| 7,071,568 B1 | 7/2006 | St. Amand et al. | |
| 7,081,648 B2 | 7/2006 | Tsai | |
| 7,101,731 B2 | 9/2006 | Karnezos | |
| 7,132,311 B2 | 11/2006 | Akiba et al. | |
| 2002/0130404 A1 | 9/2002 | Ushijima et al. | |
| 2003/0113952 A1 | 6/2003 | Sambasivam et al. | |
| 2003/0153134 A1 | 8/2003 | Kawata et al. | |
| 2004/0061213 A1 | 4/2004 | Karnezos | |
| 2004/0212096 A1 | 10/2004 | Wang | |
| 2005/0080328 A1* | 4/2005 | Vass et al. ..................... | 600/407 |
| 2005/0113651 A1* | 5/2005 | Wood et al. ................... | 600/300 |
| 2006/0043556 A1 | 3/2006 | Su | |
| 2006/0138631 A1 | 6/2006 | Tao et al. | |

OTHER PUBLICATIONS

Zhn F. Wang et al. Cardiovascular Shunts: MR Imaging Evaluation. RadioGraphics 2003; 23:S181-S191. Oct. 2003.*
Program for the SPIE Medical Imaging Conference, Feb. 17-22, 2007 http://www.spie.org/Conferences/Programs/07/mi/mi07_final.pdf.
"Computer Aided Septal Defect Diagnosis and Detection", S. Li, I.D. Ross, S. Gill, T. M. Peters, R. N. Rankin, Feb. 22, 2007.

* cited by examiner

*Primary Examiner* — Tse Chen
*Assistant Examiner* — Mark Remaly (57) ABSTRACT

Certain embodiments of the present invention provide systems and methods for detecting septal defects. In an embodiment, the method may include acquiring gated MRI data and heart atlas data. A registration of the gated MRI data and the heart atlas data may be performed as well as a flow-balance measurement. An atrial septal detection and ventricular septal detection may be performed, as well as a septal measurement. A diagnostic report may be generated detailing the location and properties of the septal defects. A physician may utilize the diagnostic report for surgery planning. After surgery, the diagnostic report may be compared with a post-surgery diagnostic report to determine the success of the surgery.

13 Claims, 5 Drawing Sheets

SYSTEM AND METHOD FOR COMPUTER AIDED SEPTAL DEFECT DIAGNOSIS AND SURGERY FRAMEWORK

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to a system and method for improved workflow of a medical imaging system. Particularly, the present invention relates to a more efficient system and method for diagnosing, planning surgery, and post surgery follow up for septal defects.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

An example of a medical diagnostic imaging system is Picture Archival Communication Systems (PACS). PACS is a term for equipment and software that permits images, such as x-rays, ultrasound, CT, MRI, EBT, MR, or nuclear medicine for example, to be electronically acquired, stored and transmitted for viewing. Images from an exam may be viewed immediately, stored, or transmitted. The images may be viewed on diagnostic workstations, by users, for example radiologists. In addition to viewing the images, the user may also view patient information associated with the image, for example the name of the patient or the patient's sex.

Many PACS systems are used as part of diagnosis. For example, a PACS may be used with cardiac imaging in diagnosing cardiovascular disease. Gated MR imaging may be used in the diagnosis of septal defects and surgery. Currently, for diagnosis, the radiologist needs to utilize two markers to measure the unbalance of in and out blood flow. A time-consuming manual search is then performed to locate the septal defects.

For surgery, the surgeon generally has to again manually locate the septal defects during surgery planning and during surgery. After surgery, the radiologist generally performs the above process manually again. When an echocardiogram is used, the time—consumption is even greater since it takes a relatively long time to locate the defect positions, which adds extra pain to the patient, especially after surgery.

Accordingly, a need exists for a system and method that may be utilized to assist in the detection of septal defects. Such a system and method may be used to detect the location and measure the size of the defect. Such a system and method may be used to provide a surgeon information for surgery planning. Such a system and method may be used to follow up after surgery to determine a level of success.

SUMMARY OF THE INVENTION

Certain embodiments of the present invention may include a method for detecting a septal defect. The method may include acquiring gated MRI data and heart atlas data. The method may also include performing a registration of gated MRI data and heart atlas data. The registration of the gated MRI data and the heart atlas data may include performing a registration of a first set of 3D volume images of the gated MRI data and the heart atlas data for the voxels of the gated MRI data. The registration may also include performing a registration of a second set of 3D volume images of the gated MRI data and the heart atlas data for heart wall voxels of the gated MRI data. The method may also include performing a flow-balance measurement. The method may also include performing atrial septal detection and ventricular septal detection. The method may also include performing septal measurement. The method may also include reporting output information in a diagnostic report. IN an embodiment, the diagnostic report may include the following properties for each defect: maximal size, minimal size, the location of the defect, whether the defect is an atrial septal defect or a ventricular septal defect. The diagnostic report may also include the ability to visualize the defects. The diagnostic report may be used for surgery planning. A post-surgery diagnostic report may be generated after surgery. The post-surgery diagnostic report and the diagnostic report may be compared to determine the success of the surgery.

Certain embodiments of the present invention may include a system for detecting a septal defect. The system may include a computer unit for manipulating data. The computer unit may execute computer software for acquiring gated data and heart atlas data. The computer unit may perform a registration of gated data and heart atlas data. The computer unit may also perform a flow-balance measurement. The computer unit may also perform atrial septal detection and ventricular septal detection. The computer unit may also perform septal measurement and report output information in a diagnostic report. The system may also include an input unit for receiving input from a user and a display unit for displaying information to a user. In an embodiment, the diagnostic report is stored in the computer unit. In an embodiment, the computer unit, input unit, and display unit comprise a picture archival communication system. In an embodiment, the gated data is acquired using magnetic resonance imaging. In an embodiment, the gated data is acquired using an echocardiogram.

Certain embodiments of the present invention may include a computer-readable storage medium including a set of instructions for a computer. The set of instructions may include an acquisition routine for acquiring gated MRI data and heart atlas data. The set of instructions may also include a registration routine for performing a registration of gated MRI data and heart atlas data. The registration routine may include performing a registration of a first set of 3D volume images of the gated MRI data and the heart atlas data for the voxels of the gated MRI data and performing a registration of a second set of 3D volume images of the gated MRI data and the heart atlas data for heart wall voxels of the gated MRI data. The set of instructions also include a flow-balance routine for performing a flow-balance measurement. The set of instructions also include a detection routine for performing atrial septal detection and ventricular septal detection. The set of instructions also include a septal measurement routine for performing septal measurement. The set of instructions also include a diagnostic routine for reporting output information in a diagnostic report. In an embodiment, a post-surgery diagnostic report may be generated after surgery. The post-surgery diagnostic report and the diagnostic report may be compared to determine the success of the surgery.

DETAILED DESCRIPTION OF THE INVENTION

Figure 1:
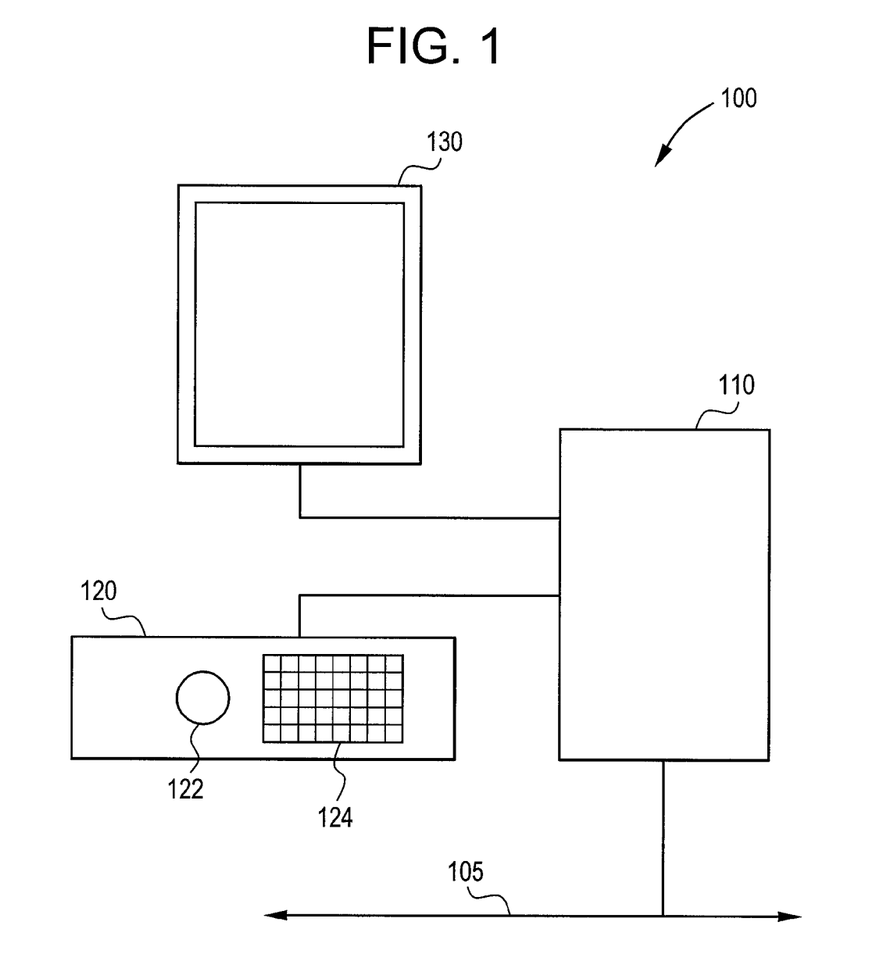
FIG. 1 illustrates an example of a system that may be used in accordance with an embodiment of the present invention.

FIG. 1 illustrates a system 100 for manipulating and displaying medical images. The system 100 includes a computer unit 110. The computer unit 110 may be any equipment or software that permits electronic medical images, such as x-rays, ultrasound, CT, MRI, gated MRI, EBT, MR, or nuclear medicine for example, to be electronically acquired, stored, or transmitted for viewing and operation. The computer unit 110 may receive input from a user. The computer unit 110 may be connected to other devices as part of an electronic network. In FIG. 1, the connection to the network is represented by line 105. The computer unit 110 may be connected to network 105 physically, by a wire, or through a wireless medium. In an embodiment, the computer unit 110 may be, or may be part of, a picture archival communication system (PACS).

The system 100 also includes an input unit 120. The input unit 120 may be a console having a track ball 122 and keyboard 124. Other input devices may be used to receive input from a user as part of the input unit 120. For example a microphone may be used to receive verbal input from a user. The system 100 also includes at least one display unit 130. The display unit 130 may be a typical computer display unit. The display unit 130 may be in electrical communication with the computer unit 110 and input unit 120. In an embodiment, the display unit 130 may represent multiple display units or display regions of a screen. Accordingly, any number of display units may be utilized in accordance with the present invention.

In an embodiment, the system 100 is a PACS with display unit 130 representing the display unit of PACS. The computer unit 110 may represent equipment and components of a PACS system other than the display unit. The computer unit 110 and display unit 130 may be separate units or be part of a single unit. In the case of separate units, the display unit 130 may be in electrical communication with the computer unit 110. The components of the system 100 may be single units, separate units, may be integrated in various forms, and may be implemented in hardware and/or in software.

In an embodiment, the computer unit 110 may be connected to a medical diagnostic imaging system by the network 105. In an embodiment, the medical diagnostic imaging system may include, for example, an x-ray system, a computerized tomography (CT) system, an ultrasound system, an electron beam tomography (EBT) system, or a magnetic resonance (MR) system.

In an embodiment, the computer unit 110 may receive gated MR cardiac images from an MR system. The gated MR cardiac images may be images captured of a patient's heart. The computer unit 110 may process the gated MR cardiac images using computer software for detecting septal defects.

Figure 2:
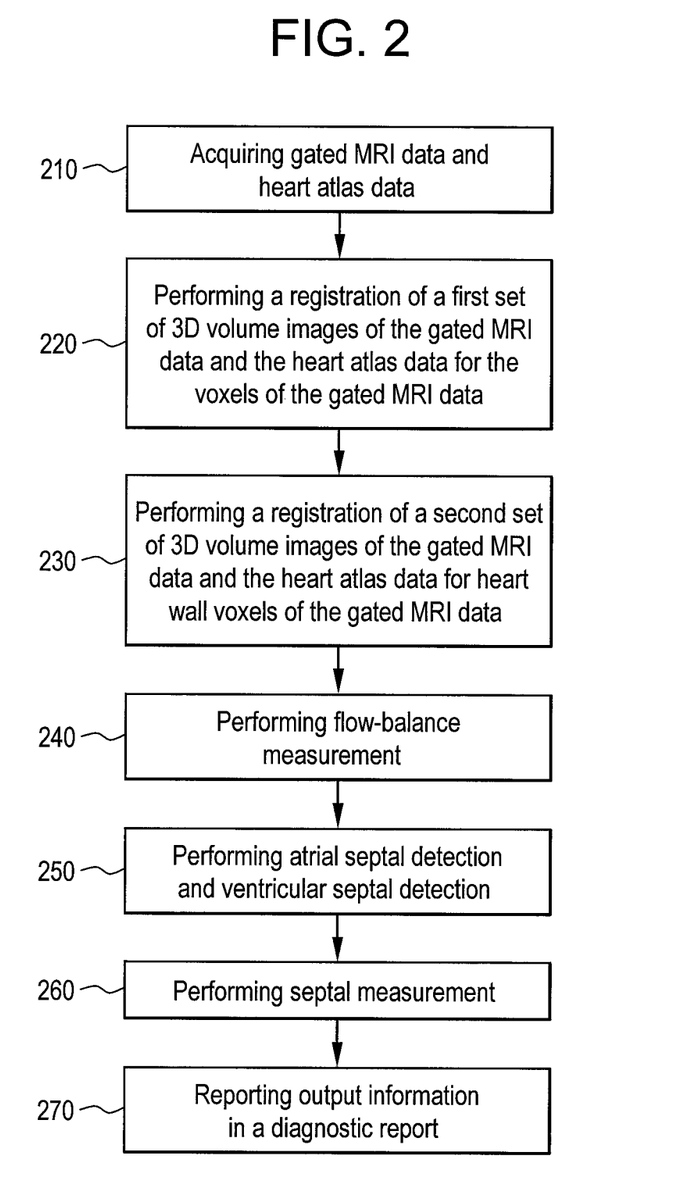
FIG. 2 illustrates a method that may be used in accordance with an embodiment of the present invention.

FIG. 2 illustrates a method 200 for detecting septal defects using computer software in accordance with an embodiment of the present invention. The method 200 conducts a registration between a pre-computed heart atlas and gated MRI (3D) sequence (4D (3D+t)) so that heart wall can be tracked. The computer software may be executed as part of the computer unit 110, or may be executed on other processing equipment. At step 210, the computer software may utilize gated MR cardiac images as input. The gated MR images may be acquired by a diagnostic imaging system, such as an MR system. The gated MR cardiac images may be retrieved from a storage mechanism, such as a database, or from other memory structure within the computer unit 110. In an embodiment, the gated MR cardiac images may be streamed from the MR equipment and processed by the computer software. In such a manner, the computer software may process the MR cardiac images as soon as the computer unit 110 receives the images. The results of the processing may then be stored and available for immediate retrieval by the user. Also at step 210, heart atlas data may also be acquired. The heart atlas data may be pre-computed and previously stored. The heart atlas data may be acquired from a memory device, such as a database, or other memory structure.

At step 220, a registration of the gated MRI data and the heart atlas data is performed for the voxels of the gated MRI data. The registration of the gated MRI data and the heart atlas data may indicate the differences between the heart atlas and the actual patient data. In an embodiment, a full registration may be performed for the gated MRI data with the heart atlas data. Alternatively, in an embodiment, an optimization routine may be performed. The optimization routine may include registering the first set of 3D volume images with the heart atlas data. The heart walls may then be segmented based on the atlas. For subsequent sets of 3D volume images, a full registration is not performed. In an embodiment, a registration is performed only for the heart walls. Accordingly, once a registration the first set of 3D volume images is performed, only a registration of the heart walls is performed in subsequent 3D volume images. Such an optimization routine may improve the efficiency and accuracy of the algorithm. In FIG. 2, the optimization routine is identified by step 230.

At step 240, a flow-balance measurement may be performed. In conducting the flow-balance measurement, two markers may be identified to measure the amount of blood pumped into and out of the heart. Based on the balance of the blood flow, it may be determined whether a defect exists. If it is determined by the flow-balance measurement of step 240 that a defect exists, an atrial septal detection and a ventricular septal detection are performed at step 250. At step 260, an atrial septal measurement may be performed. The sizes of the defects may be measured according to the maximal and minimal radius during the heart-beating circle.

At step 270, a diagnostic report on the location and characteristics of the septal defects may be generated. The diagnostic report may include the following properties for each defect: maximal and minimal size, (since the size changes while the heart is beating), location of the defect, whether the defect is ASD or VSD. The diagnostic report may also include the ability to visualize the defects. In an embodiment, the output information may be reported to a display screen, such as display screen 130. In an embodiment, the output information may be saved to a file for review, such as the patient's electronic medical record file.

Figure 3:
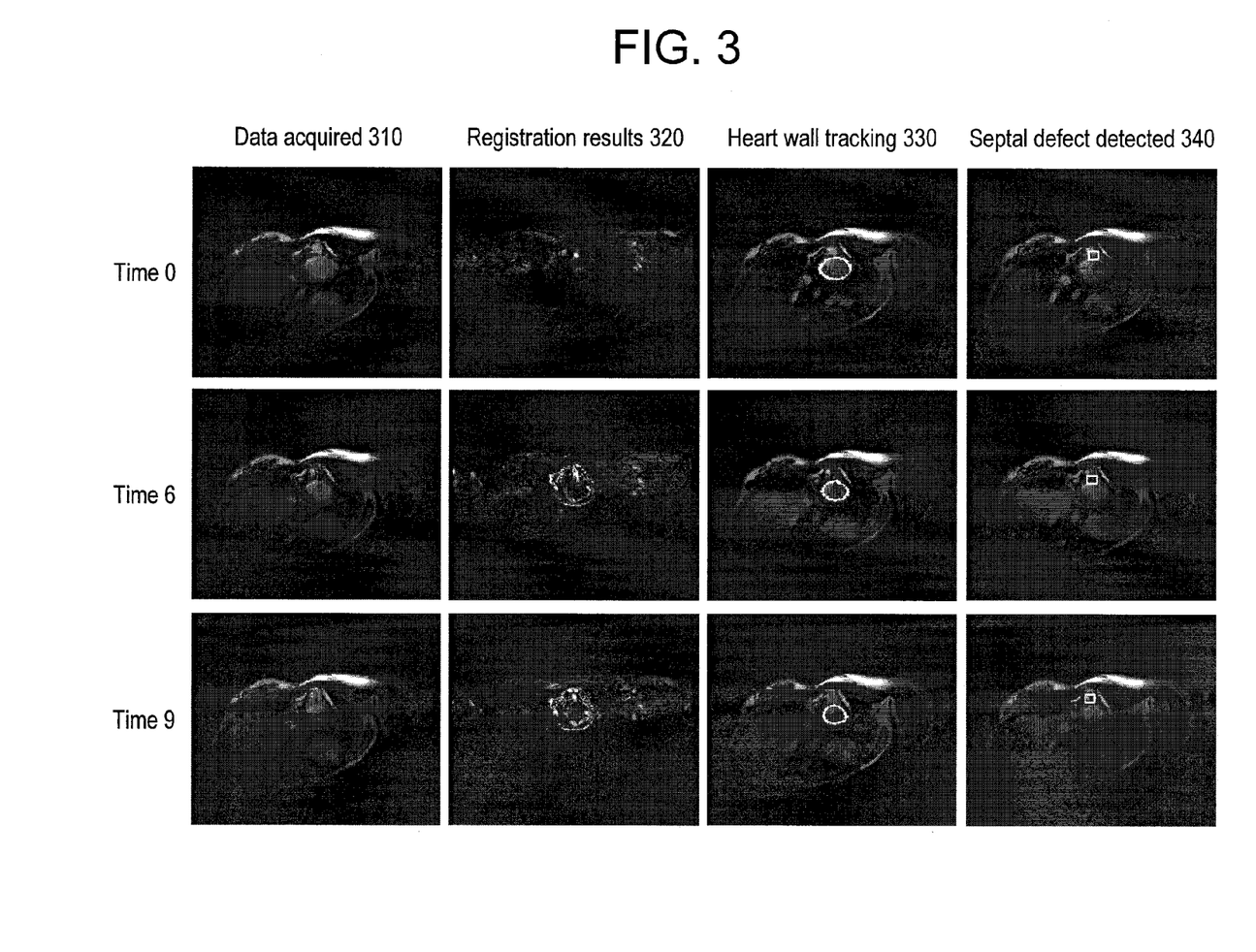
FIG. 3 illustrates an example of an application in accordance with an embodiment of the present invention.

FIGS. 3 and 4 illustrate an example and application of the method 200 in accordance with an embodiment of the present invention. The columns of FIG. 3 illustrate four stages from the method 200. The rows of FIG. 3 illustrate three different time periods captured during the heart-cycle, Time 0, Time 6, and Time 9. FIG. 4 illustrates the profile lines for the columns of FIG. 3. The profile line (a) of FIG. 4 corresponds to column 1 in FIG. 3. The profile line (b) of FIG. 4 corresponds to column 2 in FIG. 3. The profile line (c) of FIG. 4 corresponds to column 3 in FIG. 3. The profile line (d) of FIG. 4 corresponds to column 4 in FIG. 3.

Figure 4A:
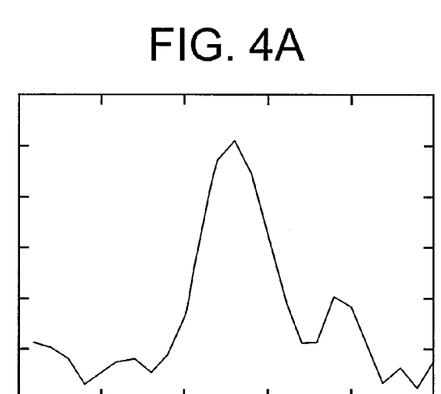
FIG. 4 illustrates an example of an application in accordance with an embodiment of the present invention.
Figure 4B:
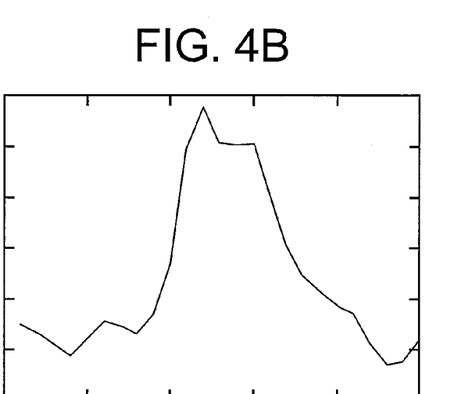
Figure 4C:
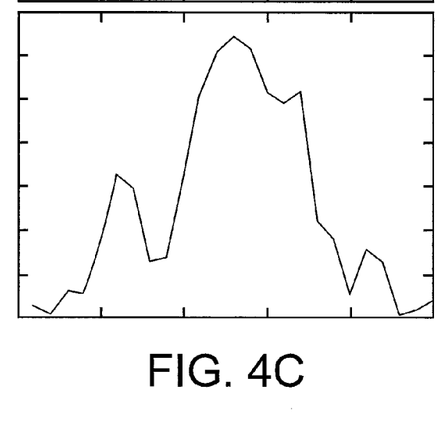
Figure 4D:
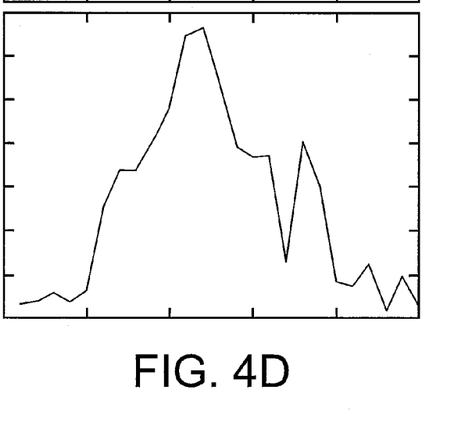

In the example of FIG. 3, Column 1 (310) illustrates the acquired data, such as the gated MR data. In the corresponding profile line of FIG. 4 (a), the maximum peak indicates the possibility of a defect. Column 2 of FIG. 3 (320) illustrates the registration of the data acquired in column 1 of FIG. 3 (the gated MR data) with the heart atlas data. In FIG. 4(b), the registration indicates the maximal difference between the actual data acquired from the patient and the heart atlas data. Accordingly, the maximal value indicates the existence of a defect.

In Column 3 of FIG. 3 (330), the location of the defect on the heart wall is displayed. The location of the defect on the heart wall is illustrated with the highlighted circle. In the corresponding graphic in FIG. 4(c), the location and size of the defect as identified on the heart wall may be illustrated. In Column 4 of FIG. 4 (340), the septal defect is identified. In the example of FIG. 4, the septal defect is identified by a square illustrated on the heart image.

Figure 5:
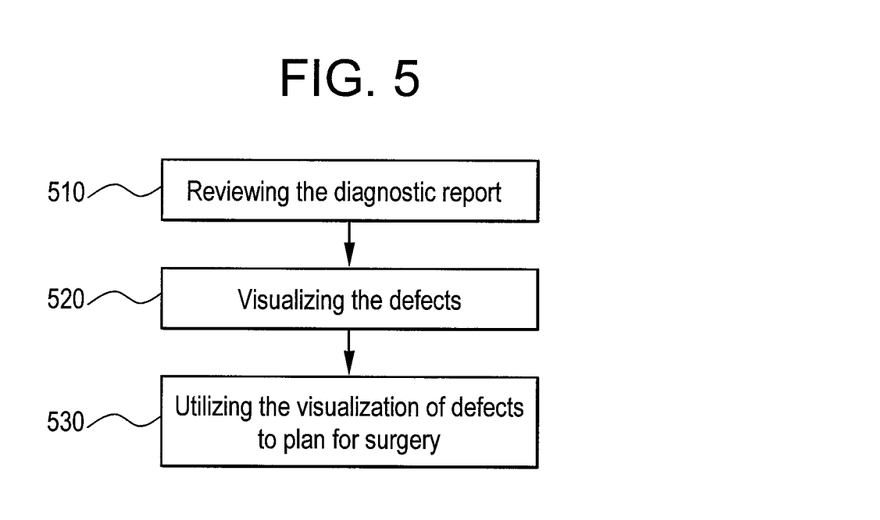
FIG. 5 illustrates a method that may be used in accordance with an embodiment of the present invention.

Once the diagnostic report has been generated and septal defects located, a physician is able to review the information and diagnostic report for surgery planning. FIG. 5 illustrates a method 500 for surgery planning utilizing the diagnostic report generated by the method 200, in accordance with an embodiment of the present invention. At step 510, a physician may retrieve and review the diagnostic report information detailing the location and characteristics of the defects. The diagnostic report may be retrieved from a storage unit, such as a database. In an embodiment, the diagnostic report is retrieved from a patient's electronic medical record. The diagnostic report may be visualized on the system 100, and in an embodiment the diagnostic report may be visualized on a PACS unit. At step 520, a physician may visualize the defects located as part of the method 200. The visualization of the defects may be highlighted for the physician's review. At step 530, a physician may utilize the information from the diagnostic report, including the visualization of the defects, for planning the surgery. The physician may utilize the diagnostic report to make decisions regarding, for example, what kind of surgery is needed, what types of occluder, is needed, what type of seal is needed, and other decisions that are generally made prior to surgery. The physician may then generate a surgical plan report based on the surgical planning. In an embodiment, the surgical plan report may be saved as part of the patient's electronic medical record. Alternatively, the surgical plan report may be saved in data structure other than the electronic medical record.

Figure 6:
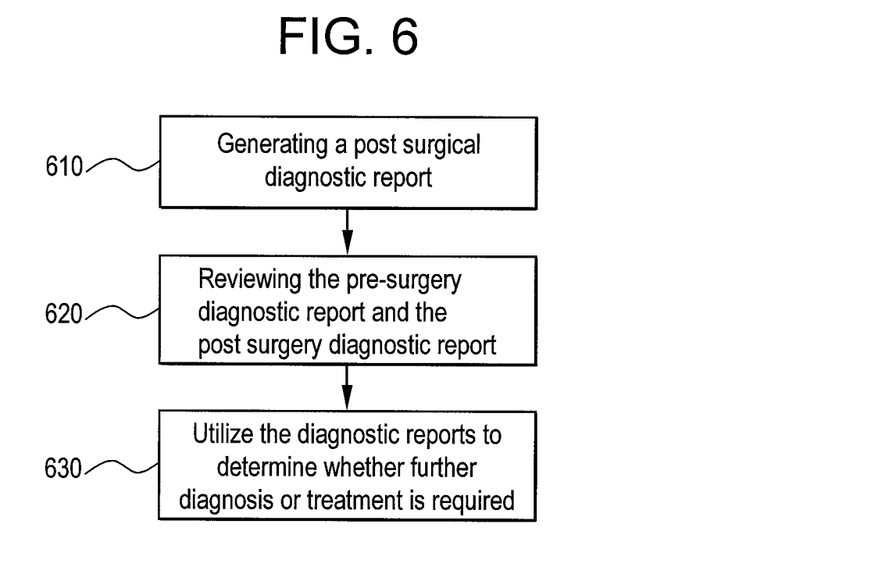
FIG. 6 illustrates a method that may be used in accordance with an embodiment of the present invention.

After the physician performs the surgery, a post surgery report may be written. The post surgery report may include the surgeon's notes and other information detailing the surgery. In an embodiment, the surgery report may be saved as part of the patient's electronic medical record. In an embodiment, a follow up examination may be performed to determine the success of the surgery. FIG. 6 illustrates a method 600 for determining the success of the surgery in accordance with an embodiment of the present invention.

At step 610, the method 200 is executed after the surgery to visualize the success of the repair of the defects. At step 610, post surgery 3D volume images are captured and a post surgery diagnostic report is generated. The post surgery diagnostic report may be saved as part of the patient's electronic medical record. At step 620, a physician may review the pre-surgery diagnostic report and the post surgery diagnostic report. The physician may compare the diagnostic reports to determine a level of success of the surgery. The physician may also review the post surgery report. In an embodiment, the physician may review the diagnostic reports on the system 100. In an embodiment, the physician may review the diagnostic reports on a PACS system. The location of the defects on the images acquired before surgery may be visualized and compared to the location of the defects on the images acquired after surgery. In such a manner, a user may determine whether the defects have been resolved. At step 630, the physician may utilize the diagnostic reports to determine whether further diagnosis or treatment is required.

The system and methods described above may be carried out as part of a computer-readable storage medium including a set of instructions for a computer. The set of instructions may include an acquisition routine for acquiring gated MRI data and heart atlas data. The set of instructions may also include a registration routine for performing a registration of gated MRI data and heart atlas data. The registration routine may include performing a registration of a first set of 3D volume images of the gated MRI data and the heart atlas data for the voxels of the gated MRI data. The registration routine may also include performing a registration of a second set of 3D volume images of the gated MRI data and the heart atlas data for heart wall voxels of the gated MRI data. The set of instructions may also include a flow-balance routine for performing a flow-balance measurement. The set of instructions may also include a detection routine for performing atrial septal detection and ventricular septal detection. The set of instructions may also include a septal measurement routine for performing septal measurement. The set of instructions may also include a diagnostic routine for reporting output information in a diagnostic report.

The set of instructions may also include a post-surgery acquisition routine for acquiring gated MRI data and heart atlas data. The set of instructions may also include a post-surgery registration routine for performing a registration of gated MRI data and heart atlas data. The post-surgery registration routine may include performing a registration of a first set of 3D volume images of the post-surgery gated MRI data and the heart atlas data for the voxels of the post-surgery gated MRI data and performing a registration of a second set of 3D volume images of the post-surgery gated MRI data and the heart atlas data for heart wall voxels of the post-surgery gated MRI data. The set of instructions may also include a post-surgery flow-balance routine for performing a flow-balance measurement. The set of instructions may also include a post-surgery detection routine for performing atrial septal detection and ventricular septal detection. The set of instructions may also include a post-surgery septal measurement routine for performing septal measurement. The set of instructions may also include a post-surgery diagnostic routine for reporting output information in a post-surgery diagnostic report. The set of instructions may also include the step of comparing the diagnostic report with the post-surgery diagnostic report.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for detecting a septal defect of a patient, the method comprising:
    using a computer unit to perform at least the following:
    acquiring gated MRI data of actual patient anatomy and pre-computed heart atlas data;
    registering the gated MRI data with the pre-computed heart atlas data, wherein said registering indicates differences between the gated MRI data and the pre-computed heart atlas data, wherein said registering includes registering a first set of 3D volume images of the gated MRI data and the pre-computed heart atlas data for the voxels of the gated MRI data;
    performing a flow-balance measurement comprising identifying two markers used to measure the amount of blood pumped into and out of a heart of the patient;
    performing atrial septal detection and ventricular septal detection;
    performing septal measurement; and
    reporting output information in a diagnostic report.

2. The method of claim 1, further including registering a second set of 3D volume images of the gated MRI data and the pre-computed heart atlas data for heart wall voxels of the gated MRI data.

3. A method for detecting a septal defect of a patient, the method comprising:
    using a computer unit to perform at least the following:
    acquiring gated MRI data of actual patient anatomy and pre-computed heart atlas data;
    registering the gated MRI data with the pre-computed heart atlas data, wherein said registering indicates differences between the gated MRI data and the pre-computed heart atlas data;
    performing a flow-balance measurement comprising identifying two markers used to measure the amount of blood pumped into and out of a heart of the patient;
    performing atrial septal detection and ventricular septal detection;
    performing septal measurement; and
    reporting output information in a diagnostic report, wherein the diagnostic report includes the following properties for each defect: maximal size, minimal size, the location of the defect, whether the defect is an atrial septal defect or a ventricular septal defect.

4. A method for detecting a septal defect of a patient, the method comprising:
    using a computer unit to perform at least the following:
    acquiring gated MRI data of actual patient anatomy and pre-computed heart atlas data;
    registering the gated MRI data with the pre-computed heart atlas data, wherein said registering indicates differences between the gated MRI data and the pre-computed heart atlas data;
    performing a flow-balance measurement comprising identifying two markers used to measure the amount of blood pumped into and out of a heart of the patient;
    performing atrial septal detection and ventricular septal detection;
    performing septal measurement; and
    reporting output information in a diagnostic report, wherein the diagnostic report includes the ability to visualize the defects.

5. A method for detecting a septal defect of a patient, the method comprising:
    using a computer unit to perform at least the following:
    acquiring gated MRI data of actual patient anatomy and pre-computed heart atlas data;
    registering the gated MRI data with the pre-computed heart atlas data, wherein said registering indicates differences between the gated MRI data and the pre-computed heart atlas data;
    performing a flow-balance measurement comprising identifying two markers used to measure the amount of blood pumped into and out of a heart of the patient;
    performing atrial septal detection and ventricular septal detection;
    performing septal measurement; and
    reporting output information in a diagnostic report, further including:
    acquiring post-surgery gated MRI data of the actual patient anatomy and the pre-computed heart atlas data;
    registering the post-surgery gated MRI data with the pre-computed heart atlas data;
    performing a post-surgery flow-balance measurement;
    performing post-surgery atrial septal detection and post-surgery ventricular septal detection;
    performing post-surgery septal measurement; and
    reporting output information in a post-surgery diagnostic report.

6. The method of claim 5, wherein said registering the post-surgery gated MRI data with the heart atlas data includes registering a first set of 3D volume images of the post-surgery gated MRI data and the heart atlas data for the voxels of the post-surgery gated MRI data.

7. The method of claim 6, further including registering a second set of 3D volume images of the post-surgery gated MRI data and the heart atlas data for heart wall voxels of the post-surgery gated MRI data.

8. The method of claim 7, further including comparing the diagnostic report with the post-surgery diagnostic report.

9. A non-transitory computer-readable storage medium storing a set of instructions for a computer, the stored set of instructions comprising:
    an acquisition routine for acquiring gated MRI data of actual patient anatomy and pre-computed heart atlas data;
    a registration routine for registering the gated MRI data and the pre-computed heart atlas data;
    a flow-balance routine for performing a flow-balance measurement that identifies two markers the measure blood pumped into and out of a heart of a patient;
    a detection routine for performing atrial septal detection and ventricular septal detection;
    a septal measurement routine for performing septal measurement; and
    a diagnostic routine for reporting output information in a diagnostic report, wherein the registration routine includes a routine a first set of 3D volume images of the gated MRI data and the heart atlas data for the voxels of the gated MRI data.

10. The non-transitory computer readable medium of claim 9, wherein the registration routine includes a routine for registering a second set of 3D volume images of the gated MRI data and the heart atlas data for heart wall voxels of the gated MRI data.

11. A non-transitory computer-readable storage medium storing a set of instructions for a computer, the stored set of instructions comprising:
- an acquisition routine for acquiring gated MRI data of actual patient anatomy and pre-computed heart atlas data;
- a registration routine for registering the gated MRI data and the pre-computed heart atlas data;
- a flow-balance routine for performing a flow-balance measurement that identifies two markers the measure blood pumped into and out of a heart of a patient;
- a detection routine for performing atrial septal detection and ventricular septal detection;
- a septal measurement routine for performing septal measurement; and
- a diagnostic routine for reporting output information in a diagnostic report, further including:
- a post-surgery acquisition routine for acquiring gated MRI data of the actual patient anatomy and the pre-computed heart atlas data;
- a post-surgery registration routine for registering the gated MRI data and the heart atlas data;
- a post-surgery flow-balance routine for performing a flow-balance measurement;
- a post-surgery detection routine for performing atrial septal detection and ventricular septal detection;
- a post-surgery septal measurement routine for performing septal measurement; and
- a post-surgery diagnostic routine for reporting output information in a post-surgery diagnostic report.

12. The non-transitory computer readable medium of claim 11, wherein the post-surgery registration routine includes a routine for registering a first set of 3D volume images of the post-surgery gated MRI data and the heart atlas data for the voxels of the post-surgery gated MRI data and for registering a second set of 3D volume images of the post-surgery gated MRI data and the heart atlas data for heart wall voxels of the post-surgery gated MRI data.

13. The non-transitory computer readable medium of claim 11, further including a comparison routine for comparing the diagnostic report with the post-surgery diagnostic report.

\* \* \* \* \*

UNITED STATES PATENT AND TRADEMARK OFFICE
CERTIFICATE OF CORRECTION

| | | |
|---|---|---|
| PATENT NO. | : 8,700,126 B2 | Page 1 of 1 |
| APPLICATION NO. | : 11/622272 | |
| DATED | : April 15, 2014 | |
| INVENTOR(S) | : Shuo Li and Sukhdeep Gill | |

It is certified that error appears in the above-identified patent and that said Letters Patent is hereby corrected as shown below:

On the title page, item (75) "Inventors: Shou Li," delete "Shou Li" and insert -- Shuo Li --.

Signed and Sealed this
Twenty-first Day of July, 2015

Michelle K. Lee
*Director of the United States Patent and Trademark Office*